US 6,607,516 B2

(12) United States Patent
Cinelli et al.

(10) Patent No.: US 6,607,516 B2
(45) Date of Patent: Aug. 19, 2003

(54) DISPOSABLE HUMAN WASTE MANAGEMENT DEVICES WITH IMPROVED ADHESIVE FLANGE TO FACILITATE ADHESION IN OILY CONDITIONS

(75) Inventors: Fabio Cinelli, Bologna (IT); Antonello Colaianni, Pescara (IT); Adelia Alessandra Tordone, Pescara (IT); Hugh Semple Munro, Chipping Camden (GB); Brian John Tighe, Aston Triangle (GB)

(73) Assignee: The Procter & Gamble Company, Cincinnati, OH (US)

( * ) Notice: Subject to any disclaimer, the term of this patent is extended or adjusted under 35 U.S.C. 154(b) by 67 days.

(21) Appl. No.: 09/917,064

(22) Filed: Jul. 27, 2001

(65) Prior Publication Data

US 2002/0128614 A1 Sep. 12, 2002

Related U.S. Application Data

(63) Continuation of application No. PCT/US00/02768, filed on Feb. 2, 2000.

(30) Foreign Application Priority Data

Feb. 2, 1999 (EP) .............................. 99102050

(51) Int. Cl.$^7$ ................................. A61F 13/15
(52) U.S. Cl. .................. 604/385.19; 604/355
(58) Field of Search ................ 604/327, 332, 604/336, 338, 339, 344, 355, 385.19

(56) References Cited

U.S. PATENT DOCUMENTS

| 3,577,989 A | | 5/1971 | Anderson |
| 4,650,817 A | * | 3/1987 | Allen et al. ................ 523/105 |
| 4,699,146 A | | 10/1987 | Sieverding |
| 4,784,656 A | | 11/1988 | Christian |
| 5,015,244 A | | 5/1991 | Cross |
| 5,173,302 A | | 12/1992 | Holmblad et al. |
| 5,176,956 A | * | 1/1993 | Jevne et al. ................ 600/391 |
| 5,423,783 A | * | 6/1995 | Battles et al. ............... 604/344 |
| 5,429,626 A | * | 7/1995 | Fenton ........................ 604/339 |
| 5,433,715 A | * | 7/1995 | Tanzer et al. ............... 604/368 |
| H1602 H | | 10/1996 | Brock |
| 5,629,079 A | * | 5/1997 | Battles et al. ................. 442/60 |
| 5,670,557 A | | 9/1997 | Dietz et al. |
| 6,198,017 B1 | | 3/2001 | Basedow et al. |

FOREIGN PATENT DOCUMENTS

| CH | 643730 A1 | 11/1980 |
| EP | 245064 A2 | 11/1987 |
| EP | 184470 B1 | 4/1991 |
| EP | 554106 A1 | 8/1993 |
| EP | 753290 A2 | 1/1997 |
| EP | 638303 B1 | 11/1997 |
| EP | 850625 A1 | 7/1998 |
| EP | 850649 A1 | 7/1998 |
| EP | 855190 A1 | 7/1998 |

(List continued on next page.)

*Primary Examiner*—Weilun Lo
*Assistant Examiner*—Michael Bogart
(74) *Attorney, Agent, or Firm*—Peter D. Meyer

(57) ABSTRACT

The present invention relates to a disposable human waste management devices such as fecal and urine management devices (10) which are provided with adhesives for attachment of the device to the skin. In particular the present invention relates to adhesives (20) which provide secure attachment and are pleasing to the skin upon application, yet cause no discomfort upon removal. In particular the present invention relates to adhesives which provide secure attachment to oily and greasy skins. Preferably the adhesive also provides secure attachment under moist and wet skin conditions and which maintains adhesive peel strength even under exposure to excess water.

19 Claims, 4 Drawing Sheets

FOREIGN PATENT DOCUMENTS

| | | |
|---|---|---|
| EP | 676457 B1 | 10/1998 |
| EP | 888786 A2 | 1/1999 |
| GB | 1078588 | 5/1966 |
| GB | 2115431 A1 | 9/1983 |
| GB | 2152387 A1 | 8/1985 |
| WO | WO 93/10201 A1 | 5/1993 |
| WO | WO 95/16424 A1 | 6/1995 |
| WO | WO 95/20634 A1 | 8/1995 |
| WO | WO 96/13238 A1 | 5/1996 |
| WO | WO 96/33683 A1 | 10/1996 |
| WO | WO 97/05171 A1 | 2/1997 |
| WO | WO 97/24149 A1 | 7/1997 |
| WO | WO 98/03208 A1 | 1/1998 |
| WO | WO 98/28017 A1 | 7/1998 |
| WO | WO 99/00092 A1 | 1/1999 |
| WO | WO 00/45766 A1 | 8/2000 |
| WO | WO 00/45863 A1 | 8/2000 |
| WO | WO 00/45865 A1 | 8/2000 |
| WO | WO 00/45866 A1 | 8/2000 |

\* cited by examiner

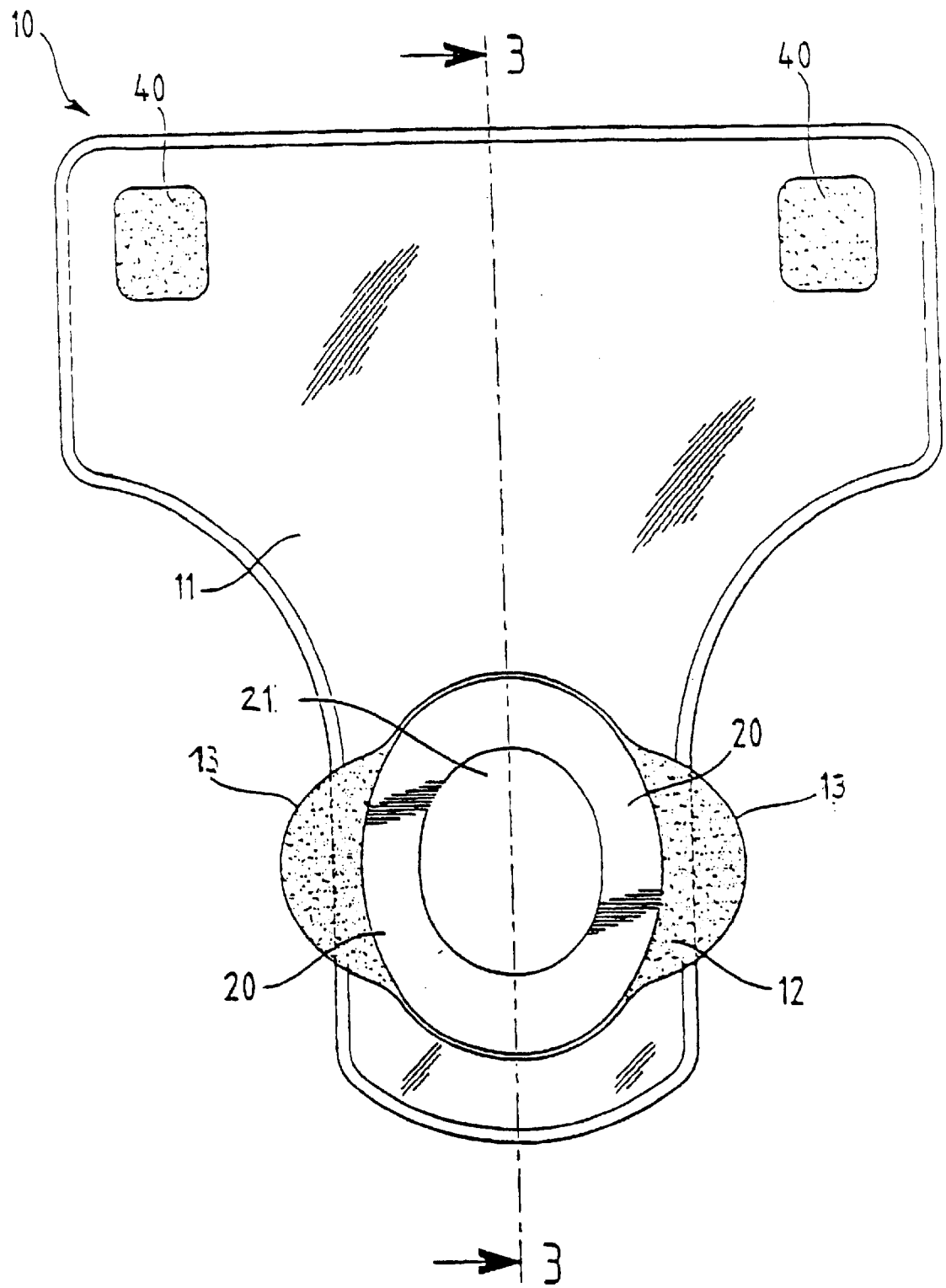

DISPOSABLE HUMAN WASTE MANAGEMENT DEVICES WITH IMPROVED ADHESIVE FLANGE TO FACILITATE ADHESION IN OILY CONDITIONS

PRIOR APPLICATION

This application is a continuation of PCT Application No. PCT/US00/02768 filed on Feb. 2, 2000 and published in English.

FIELD OF THE INVENTION

The present invention relates to a disposable human waste management devices such as urine management devices and faecal management devices for babies, children or adults to be attached directly to the skin between the buttocks of the wearer. The device utilises an improved adhesive so as to facilitate easy application and removal of the device from the wearer, whilst ensuring maintenance of the device in the desired position. In particular the adhesives provide attachment on greasy and oily skin.

BACKGROUND OF THE INVENTION

Urine and faecal management devices are known articles of manufacture that are designed to be worn principally by incontinence sufferers and in particular by bedridden patients. Such devices are attached to the natural anal region or artificial anus of the wearer and or uro genital area and are intended to receive entrap and immediately contain urine, faecal material and other bodily discharges.

Such devices as they are mostly known today are designed to be worn by bedridden patients. As such the devices are constituted of a relatively long and narrow tube, at one extremity of which there is an aperture and a skin attachment device upon which an adhesive can be applied.

Examples of these bags are disclosed for example in U.S. Pat. No. 3,577,989, which details a disposable elimination-trapping bag for incontinence sufferers including a container member having an open-top portion, and a flange secured to the container member around the open-top portion. The flange may include a layer of adhesive on its surface as a means of attachment of the bag to the wearer or alternatively discloses the use of elastic straps to attach the bag to the wearer. U.S. Pat. No. 4,784,656 also describes a receptacle for collecting faecal matter from incontinence sufferers. The faecal collector comprises a gasket, conduit means or a cylinder and a receptacle; the receptacle and conduit means are each formed from two sheets of odour barrier thermoplastic film that are heat sealed along their side edges, respectively and the side surface of the gasket is coated with a layer of adhesive; GB 2 152 387, teaches a faecal collector for incontinence sufferers comprising a collection bag and a ring, which is provided with an adhesive. The faecal collector comprises a pair of panels of thermoplastic sheet material joined at their margins to define an elongate bag having an opening at one end. GB 1 078 588 describes a urine collector comprising a liquid proof bag of tube like configuration having an opening surrounded by an attachment means in the form of an adhesive bearing material.

Other types of faecal management bags having a flatter shape are known from EP 245 064. EP 245 064 discloses bags having a front and a rear wall, the front wall containing the aperture and attachment means to the body. The attachment means is a skin compatible water resistant material such as a hydrocolloid and a water insoluble viscose elastic binder.

Due to their typical elongated shape and dimensions, such devices particularly when worn by active wearers, such as infants or non bedridden incontinent adults, can readily twist around the thighs of the wearers and/or can cause the formation of folds and kinks in the devices themselves. Under such circumstances the pressure and stress exerted upon the bag will naturally increase due to the movement of the wearer and the pressure of the wearer's body upon the bag. Consequently, the likelihood that the urine or faecal material once excreted and contained within the bag will be caused to exert pressure upon the attachment means of the device will increase. As a result not only will the storage capacity of the device be detrimentally affected but also more importantly it may result in unintentional detachment of the device from the wearer during use. Such an occurrence is unacceptable causing distressing consequences for both the wearer and the carer.

Hence, it is critical that the urine and/or faecal management devices are designed such that they are securely attached to the skin of the wearer and do not become unintentionally unattached during all circumstances of use.

In order to provide the desired level of adhesion of the device to the wearer, the prior art typically discloses the utilisation of certain adhesives having very high cohesive strengths such as rubber based adhesives and acrylics. These adhesives are then applied as thick layers over the entire surface of the flange of the device to maximise the adhesive force by which the device is secured to the skin of the wearer. Indeed it is apparent that these devices, and in particular the adhesives, have been designed for use on faecal management devices utilised by bedridden patients particularly those having an artificial anus whereby maximum adhesion takes priority over any other criteria such as patient comfort.

However, the adhesive must have a skin compatible composition and not be harsh or aggressive towards the skin or cause skin irritation or inflammation. Also it is preferred if the adhesive is compliant with the skin of the wearer such that maximum skin surface contact between the adhesive and the skin is achieved. Moreover, it is also desirable to provide an adhesive such that the disposal human waste management device can be readily removed from the wearer, without the wearer experiencing any unacceptable pain level. This is particularly important under circumstances, where the device is misplaced, and removal and reapplication of the device once or even a number of times is required and or to ensure the application of such devices on sensitive skin and wearer groups such as infants. However, on the other hand the desired level of adhesion, albeit painless should of course also be maintained during such multiple applications of the device.

The problem of achieving the desired adhesion level is further exacerbated under wet skin conditions. Typically, prior to the placement of the disposable human waste management device, the skin is cleaned and is usually as a result moist. The currently available adhesives, such as those containing hydrocolloid particles, however often do not immediately strongly adhere to the skin and may need to be held in place until sufficient minimum adhesion occurs. Moreover, the overall adhesive ability of such adhesives tends to be significantly reduced on wet skin surfaces per se, so that the device will typically not remain attached to the skin during wear if any pressure is exerted onto the device, for example by the movement of the wearer or during the defaecation process. Alternatively adhesives which are able to absorb water and thus immediately adhere to moist skin, tend to absorb water very rapidly and not in a controlled manner such that extended adhesion time is not provided.

Another problem which is associated with adhesives which do not maintain their adhesive strength after exposure to liquids is that not only will the adhesive no longer adhere satisfactorily to skin, it will also no longer adhere to the flange.

Moist and wet skin however is not just a problem which is prevalent at the device application stage, as a significant amount of moisture is also generated during the use of the device from the wearer by perspiration and from the material contained within the disposable human waste device. In addition particularly for the case of urine management devices, small amounts of liquid may be deposited or migrate on to the flange surface without entering the bag cavity. The resulting humid environment naturally further increases when the device is utilised in combination with a diaper. Under such circumstances currently available adhesives typically cannot absorb this moisture and again the adhesive strength is reduced to such an extent that the device will often become detached under exertion of pressure during wear. It is hence very important to provide an adhesive which provides both initial adhesion and maintenance of its adhesive strength on wet skin. Moreover, it is also another important factor for the product performance that the adhesive is also stable to exposure to excess quantities of liquid such as water and in particular urine, so that it will also not loose its adhesive strength under such circumstances.

Another problem which is particularly prevalent for urine and faecal management devices is the ability for the adhesive to adhere on greasy or oily skin surfaces. The levels and types grease or sebum naturally present on the skin vary from person to person. In addition the wearers of such products typically utilise creams such as moisturising creams or rash creams or other pharmaceutical creams on the area of skin typically in contact with the adhesive of the device. Thus it is also desirable that the adhesive exhibits an ability to adhere to greasy skin.

None of the prior art in the field of faecal management bags however even recognises or addresses the problem of providing these devices with an adhesive which meets these criteria, in particular adhesives which adhere to wet skin and are stable and maintain their adhesiveness even when exposed to excessive amounts of liquid or adhesives which adhere to oily and greasy skin.

The prior art in the general field of adhesives for attachment to the skin is in contrast more developed in the field of articles such as band-aids, plasters and bandages. These articles are however typically applied in an emergency situation, where for example, a cut into the skin of the wearer has occurred and absorption of the body liquids emanating from a wound is desired. In this context performance aspects of the article such as easy application and use of the product, comfortable wear as well as painless removal, and discreteness are again subordinate, to other criteria in this case such as sterility, healing support, and mechanical protection of the wound. Such products typically have poor wet skin adhesion.

Adhesion to wet skin is addressed for example in WO 98/03208 which discloses medical pressure sensitive adhesives which can adhere to dry or wet skin and which comprise a mixture of hydrophilic (meth)acrylate copolymer containing tertiaryamino groups, a hydrophilic (meth) acrylate copolymer containing carboxyl groups, carboxylic acids and a crosslinking system. However this document does not discuss adhesion after exposure to excess liquid. Similarly, WO 97/24149 discloses a polar lipophilic pressure sensitive adhesive comprising a hydrophilic polymer matrix, a plasticizing solution and a surfactant that provides good adhesion to a variety of skin types.

Another field wherein the use of such adhesives has been disclosed is in absorbent such as for example sanitary napkins, as described in for example US statutory invention registration H1602 or WO 96/33683 and WO 95/16424. The latter discloses sanitary articles having a topical adhesive which is applied on the wearer facing side of a sanitary napkin along the entire periphery. WO 96/13238 discloses a topical adhesive which is described in terms of frequency dependency. EP-638 303 discloses the use of a topical adhesive on side cuffs of sanitary napkins in order to keep the cuffs in an upright position. Swiss publication CH-643730 discloses the use of a very long sanitary napkin having chamfered outer edges with a topical adhesive at the four corners of the outer edges in order to provide a topical adhesive area well outside the region of pubic hair growth.

However all of these disclosures typically disclose a product which is designed to be utilised in combination with an undergarment and hence the degree of adhesion actually provided is very low and is not designed to withstand any excessive pressure. Moreover the adhesive is only discussed in general terms or concentrates on the area of application of the adhesive to the article. The nature of adhesive per se other than the basic physical requirements such as pressure sensitivity are not discussed in particular with reference to the chemical composition or the adhesive criteria.

Hence there still exists a need to provide disposable human waste management devices having an adhesive for the secure attachment and painless removal of the device from the skin in-between the buttocks of the wearer so as to be suitable for use of sensitive skin of an infant and it is thus an object of the present invention to provide such a device.

It is another objective of the present invention to provide an adhesive that exhibits an ability to adhere to skin upon reapplication, particularly multiple reapplication for example when the device is misplaced, whilst still allowing painless removal.

It is another object of the present invention to provide an adhesive that will adhere to oily and greasy skin, preferably over the entire period of wear.

It is yet a further objective of the present invention that the adhesive will adhere to moist or wet skin, independent of whether this is direct application of the device onto wet skin, or moisture which is generated on the skin surface during the wearing period of the device. In particular it is an objective of the present invention to provide an adhesive which is liquid stable particularly to water and urine, such that the adhesion properties will not be significantly affected in the presence thereof over the period of wear of the device.

It is another object of the present invention to provide an adhesive which upon removal from the skin of the wearer leaves no residues. It is yet another object of the present invention to provide an adhesive which does not cause a cold or otherwise unacceptable temperature sensation upon application to the wearer.

An additional object of the present invention to provide an adhesive which in combination with the flange material provides flexibility, stretchability and contractability so that it is able to adapt to the contours of the body during all bodily movements and hence be comfortable for the wearer of the device, whilst still having sufficient adhesive capacity to ensure secure attachment during use.

It has now been surprisingly found that the above drawbacks will be substantially alleviated by providing the flange of the disposal human waste management device with an adhesive as defined hereinafter. The adhesive provides secure attachment including to moist and oily surfaces, is pleasing to the skin upon application, and yet causes no discomfort upon removal and maintains its adhesive strength over the period of wear under varying conditions.

In another aspect of the present invention, the disposal human waste management device with its specific adhesive as defined herein can be advantageously used in combination with a reusable underwear garment or preferably with a disposable diaper.

BRIEF DESCRIPTION OF THE DRAWINGS

It is believed that the invention will be better understood from the foregoing description in conjunction with the accompanying drawings in which:

FIG. 4 is a plan view of a disposable urine management device of the present invention.

SUMMARY OF THE INVENTION

Figure 1:
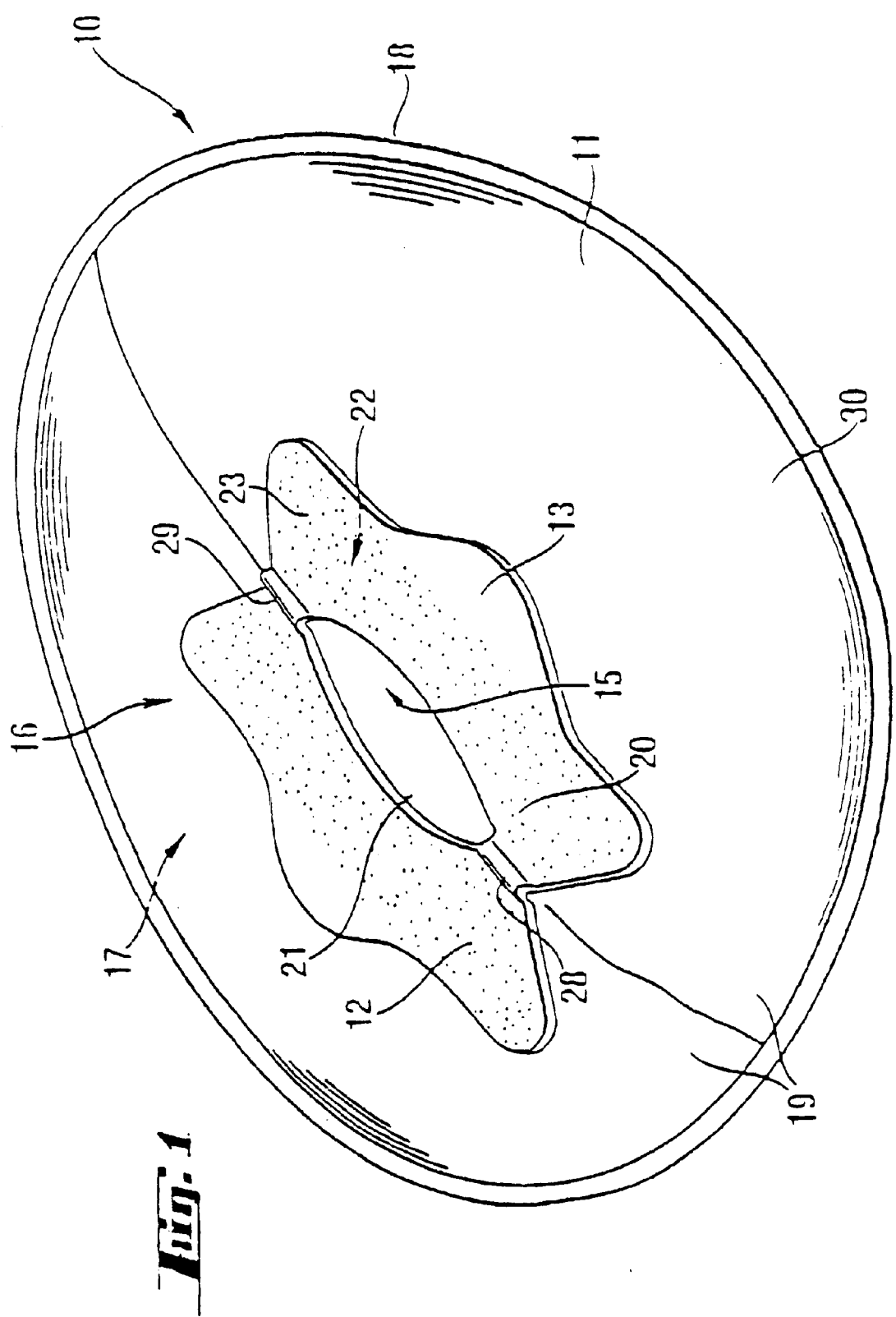
FIG. 1 is a perspective view of a disposable faecal management device in accordance with the present invention.

Any disposable human waste management device known in the art can be provided with the adhesive according to the present invention. Typically urine and faecal management devices comprise a bag (11) having an aperture (21) and a flange (12) surrounding the aperture for adhesive attachment to the uro-genital area and or the perianal area of a wearer as visible from FIG. 1. According to the present invention the adhesive is provided so as to have an initial dry skin peel strength ($P_{DI}$) and an initial greasy skin peel strength ($P_{GI}$) measured according to the test method herein, which has a ratio of $P_{DI}$ to $P_{GI}$ of from 1:1 to 1:0.2, preferably from 1:1 to 1:0.3.

According to the present invention the adhesive is also preferably provided so as to have an initial peel strength ($P_{DI}$) under normal ambient conditions and a final peel strength ($P_{WF}$) after exposure to water according to the test method described herein, whereby the ratio of $P_{DI}$ to $P_{WF}$ is from 2:1 to 1:4 preferably from 2:1.25 to 2:4 and has a water absorption capacity as defined in the test herein of at least 3% by weight of said adhesive.

The adhesive allows attachment of disposable human waste management devices to the skin of the wearer, the adhesive being provided as a layer having a certain thickness or calliper C measured in millimeters (mm), typically on at least part of the wearer facing surface of the flange.

Detailed analysis of the sequence of common situations occurring from the application of a faecal management device to the time of removal of such a device has shown that specific adhesive characteristics need to be preferably satisfied in order to achieve the desired performance objectives, in particular to secure initial attachment, secure attachment during use and painless removal after wear. The characteristics which have been considered in this context are the elastic modulus describing the elastic behaviour of the material and the viscous modulus which describes the viscous behaviour of the adhesive material.

The viscous behaviour of the adhesive can be interpreted to represent an indication of the ability of the adhesive to quickly attach and securely adhere to a particular surface. The elastic behaviour can be interpreted as an indication of the "hardness" behaviour of the adhesive. Its value is also important for good initial attachment. Their combination is believed to be an indicator of the required force upon removal. The relation between elastic and viscous modulus is considered to be an indication on which fraction of the removal energy will be dissipated within the adhesive and which fraction is available to trigger the actual removal.

In order to provide topical adhesives for secure initial and prolonged attachment and easy/painless removal the relation between the elastic modulus and the viscous modulus as well as their dynamic behaviour is also of importance.

The adhesive has an elastic modulus at a temperature of 37° C. (100° Fahrenheit) abbreviated $G'_{37}$, a viscous modulus at a temperature of 37° C. (100° Fahrenheit) of $G''_{37}$, and a viscous modulus at a temperature of 25° C. (77° Fahrenheit) of $G''_{25}$.

The adhesive according to the present invention preferably satisfies the following conditions;

$G'_{37}$ (1 rad/sec) is in the range 500 Pa to 20000 Pa,
preferably 700 Pa to 15000 Pa, most
preferably 1000 Pa to 10000 Pa.
$G''_{37}$ (1 rad/sec) is in the range 100 Pa to 15000 Pa,
preferably 100 Pa to 10000 Pa, most
preferably 300 Pa to 5000 Pa.
and the ratio of $G'_{37}$ (1 rad/sec)/$G''_{37}$ (1 rad/sec) is in the range of 1 to 30.

Provided the above theological conditions are satisfied the adhesives will also satisfy conditions such as sufficient cohesiveness (to prevent residue of adhesive on the skin) which are important for commercial use of such adhesives and apparent to those skilled in the art. Adhesive compositions which satisfy the above criteria can be used as adhesives for the flange provided they also satisfy the common requirements of being safe for use on human or animal skin during use and generally after disposal of the device.

Often the criteria of hygienic appearance such that adhesive compositions which are transparent or white upon application are preferred.

It has been determined that the relation between the thickness or calliper C, measured in millimeters (mm), of the layer in which the adhesive is provided, typically onto at least a portion of the wearer facing surface of the flange, and the viscous modulus $G''_{25}$ at about 100 rad/sec of the adhesive, is relevant to the scope of providing an easy and painless removal from the wearer's skin of such a adhesive applied on at least part of the wearer facing surface of a faecal management device for attachment of said device to the skin of a wearer.

The adhesive of the present invention is thus preferably provided as a layer having a thickness C such that the viscous modulus $G''_{25}$ (100 rad/sec) and the thickness C preferably satisfy the following empirical equation:

$$G''_{25} \leq [(7.00+C) \times 3000] Pa$$

and preferably also the following empirical equation:

$$G''_{25} \leq [(5.50+C) \times 1700] Pa$$

DETAILED DESCRIPTION OF THE INVENTION

According to the present invention the adhesive can be utilised on disposable human waste management devices such as a faecal or urine management devices (10) which are applied to the perianal area of a wearer as visible from FIG. 1. The word "skin" according to the present invention does not only relate to the specific derma of the user but includes the mucous tissue as well as the hair which is typically found in the genital region.

The skin of the wearer to which devices are typically applied will vary considerably from person to person. In particular the type and amount of grease or sebum produced can vary considerably from person to person. Moreover, the wearers of such devices typically will apply creams to the area of skin which will contact the adhesives. These creams may be of a purely cosmetic nature i.e. moisturing creams or may be creams used to treat certain skin conditions by which the wearer may be afflicted ranging from mild skin irritation, and diaper rash to haemorrhoids and other more serious skin afflictions. In the latter case the use of such creams plays an essential role in the treatment of wearer's condition and cannot be relinquished. It is thus important to provide an adhesive which adheres to greasy skin. Accordingly the present invention provides an adhesive having a dry initial peel strength ($P_{DI}$) and a greasy initial peel strength ($P_{GI}$) as determined by the test method described herein, where the ratio $P_{DI}$ to $P_{GI}$ is from 1:1 to 1.0:0.2, preferably from 1:1 to 1:0.3. Typically for utilisation for disposable human waste management devices the dry initial peel strength is ($P_{DI}$) is from 0.1N/cm to 7.0N/cm, preferably from 0.1N/cm to 5.0N/cm, more preferably from 0.5N/cm to 3N/cm. The value of the grease initial peel strength is preferably the same as for the dry initial peel strength. However typically a lower level is achieved and is acceptable at levels from 0.1N/cm to 5N/cm, preferably from 0.1N/cm to 3N/cm, more preferably from 0.1N/cm to 2N/cm. It is also preferable of the adhesion to greasy skin is maintained over a period of wear time.

Due to the nature and environment in which such disposable human waste management devices such as urine and faecal management devices are utilised it is also preferably a feature that the adhesive has a water absorption capacity as defined in the test herein of at least 3% by weight of said adhesive (so that the adhesive adheres directly onto wet or moist skin). In addition, it is also preferable that the adhesive maintains its adhesive strength in the presence of excess liquid for example when the wearer of the device urinates. In particular, the ratio of the peel strength of the adhesive as determined in the test methods herein should most preferably be maintained at a constant value such that the ratio of initial peel strength ($P_{DI}$) and the final peel strength ($P_{WF}$) is from 2:1 to 1:4, preferably from 2:1.25 to 2:4, most preferably from 2.0:1.5 to 2.0:2.5. Typically for disposable human waste management devices the initial peel strength for dry and more preferably also for wet skin should be from 0.1N/cm to 7.0N/cm, 0.1N/cm to 5.0N/cm, preferably from 0.5N/cm to 3.0N/cm.

It is further also preferable that the adhesive in addition to maintaining its peel strength over a period of time even in the presence of water also absorbs less than 15%, preferably less than 10%, more preferably less than 7% water. Whilst not intending to being bound by theory, it is believed that in order to obtain direct adhesion onto wet skin and maintain constant adhesion performance over a period of wear, even when exposed to excess liquids or high humidity the ability of the adhesive to absorb water needs to be considered. In particular, it has been identified that, not only the absolute ability of the adhesive needs to be considered, but also the rate of water absorption in order to provide an adhesive meeting the above identified performance parameters.

For example hydrocolloid particle containing adhesives which are known in the art comprising a 3-dimensional rubber matrix and colloidal absorbent particles dispersed therein are only able to absorb limited amounts of water through the colloidal particles themselves and not the matrix itself. In addition the rate at which water is absorbent is slow. Hence these prior art adhesives do not adhere to wet surfaces.

Prior art hydrogel adhesives on the other hand are able to not only absorb large quantities of water but also at a very fast rate. As a result such adhesives may be able to adhere, to wet surfaces, however due to the combination of fast rate of absorption and large absolute water uptake, these adhesives loose their adhesive strength rapidly in the presence of excess water or high humidity.

Accordingly the adhesives of the present invention exhibit both an ability to adhere directly to wet skin, by having a minimum absolute water absorption ability in combination with a rate of absorption such that the peel strength remains within defined levels over the period of wear.

The adhesive is provided with the preferred pattern, typically on the wearer facing surface (23) of the flange (12) of the device (10), as a layer having a thickness or calliper C that is preferably constant. The layer can be preferably continuous or alternatively discontinuous, e.g. in form of dots, spirals, or stripes.

Even though adhesives are used like pressure sensitive adhesives on human skin hair and mucous tissues, it is understood that the adhesive compositions could only with difficulty be considered typical pressure sensitive adhesives (referred to as PSA hereinafter) on the basis of the most characteristic Theological behaviours identifying such materials.

In fact as the person skilled in the art of adhesives knows, the most characteristic feature that distinguishes a PSA from other substances that can temporarily adhere objects (e.g. water between two glass plates could) is the fact that their rheological parameters and especially the Elastic Modulus G' vary greatly with the frequency of applied stresses. More in particular, G' of PSA can increase over some orders of magnitude, while the frequency of applied stresses varies from typical bonding frequency to typical debonding frequency, i.e. 1 rad/s to 100 rad/s as indicated below.

As a first consequence, it is therefore inadmissible to define materials intended for use as "adhesives" by giving values of rheological parameters and especially of G' at a fixed value of frequency. This can be misleading because in the absence of other characteristics such as surface chemistry it will include materials which have no practical value. It is hence necessary that rheological characterisation must be on the basis of dynamic considerations. This not only applies to the Elastic Modulus G' but also to the viscous modulus G" and hence also for tan (d)=G"/G'.

It is well known that typical PSAs have not only a high variation of G' across the considered frequencies, but also that there is an even higher variation of G" which can get close or become even higher than the value of G', i.e. tan (d) becomes about or even greater than 1, in particular at the frequencies that are typical of debonding.

Without wishing to be bound by theory this can be interpreted as meaning that a high fraction of the energy applied for the debonding is dissipated within the adhesive (so it is not effective in causing the debonding) and through the interface of the adhesive and the skin, while this fact causes macroscopically the recording of a very high level of adhesive force.

As indicated above materials useful as adhesives according to the present invention have theological characteristics which are measured at a reference temperature of 37° C. (as usual body temperature of humans) and in a range of frequencies. It has been found that upon application of a human waste management device with a adhesive the adhesive contact is formed at a low frequency, while debonding happens at the speed of removing the device. This speed is expressed as a frequency of 100 rad/s, while the low frequency of forming the adhesive bond has been found to be on the order of 1 rad/s. Therefore, the frequency range for use according to the present invention is between 1 and 100 rad/s.

In order to provide good conditions of bonding, i.e. at a frequency of about 1 rad/sec, the absolute values of the elastic modulus should not be too high, otherwise the adhesive is too hard and it is not able to intimately join or mold to the surface to which it is expected to adhere. It is also important to have a low absolute value of G" in order to have good cohesion while the material remains soft and capable of gently adhering to skin.

The ratio of $G'_{37}$ (1 rad/sec) over $G''_{37}$ (1 rad/sec) is important to ensure that these two values are balanced upon adhesion to the skin.

$$\frac{G'_{37}(100 \text{ rad/sec}) - G''_{37}(100 \text{ rad/sec})}{G'_{37}(1 \text{ rad/sec}) - G''_{37}(1 \text{ rad/sec})}$$

needs to be large enough to ensure that the dynamic behaviour of both the elastic and the viscous module are maintained in a relationship which provides secure adhesion and painless and easy removal.

Finally the person skilled in the art will also recognise that the Glass Transition Temperature Tg of the adhesive composition, the specific heat capacity, and the specific heat conductivity are parameters which are useful to more fully define the group of useful adhesives.

The following set of characteristics should preferably be satisfied for the adhesive of the present invention:

preferably be less than 0° C., more preferably less than −5° C. and most preferably less than −10.

In order to provide adhesive compositions which satisfy the requirements of the above rheological and physical characteristics of an adhesive any medically suitable substantially water insoluble pressure sensitive adhesives comprising a polymer which forms a 3-dimensional matrix meeting the these characteristics may be utilised.

According to the present invention the 3 dimensional matrix also referred to herein as a gel, comprises as an essential component a polymer which can be physically or chemically cross linked. The polymer may be naturally or synthetically derived. The uncrosslinked polymer includes repeating units or monomers derived from vinyl alcohols, vinyl ethers and their copolymers, carboxy vinyl monomer, vinyl ester monomers, esters of carboxy vinyl monomers, vinyl amide monomers, hydroxy vinyl monomers, cationic vinyl monomers containing amines or quaternary groups, N-vinyl lactam monomer, polyethylene oxides, polyvinylpyrrolidone (PVP), polyurethanes, acrylics such as methyl acrylate, 2-hydroxyethyl methacrylate, methoxydiethoxyethyl methacrylate and hydroxydiethoxyethyl methacrylate, acrylamides, and sulphonated polymers such as acrylamide sulphonated polymers for example 2 acrylamido methylpropane sulphonic acid and acrylic (3-sulphopropyl) ester acid, and mixtures thereof. Also acrylonitrile, methacrylamide, N,N,-dimethylacrylamide, acrylic esters such as methyl, ethyl and butyl acrylates. Alternatively, the uncrosslinked polymer may be a homopolymer or copolymer of a polyvinyl ether, or a copolymer derived from a half ester of maleic ester. Similarly any other compatible polymer monomer units may be used as copolymers such as for example polyvinyl alcohol and polyacrylic acid or ethylene and vinyl acetate.

As another alternative, the polymers may be block copolymer thermoplastic elastomers such as ABA block copolymers such as styrene-olefin-styrene block copolymers or ethylene-propylene block copolymers. More preferably such polymers include hydrogenated grade styrol/ethylene-butylene/styrol (SEBS), styrene/isoprene/styrene (SIS), and styrol/ethylene-propylene/styrol (SEPS).

| | |
|---|---|
| $G'_{37}$ (1 rad/sec) | is in the range 500 Pa to 20000 Pa, preferably 700 Pa to 15000 Pa, most preferably 1000 Pa to 10000 Pa. |
| $G''_{37}$ (1 rad/sec) | is in the range 100 Pa to 15000 Pa, preferably 100 Pa to 10000 Pa, most preferably 300 Pa to 5000 Pa. |
| the ratio of $G'_{37}$ (1 rad/sec)/ $G''_{37}$ (1 rad/sec) | is in the range of 1 to 30. |
| the ratio $$\frac{G'_{37}(100 \text{ rad/sec}) - G''_{37}(100 \text{ rad/sec})}{G'_{37}(1 \text{ rad/sec}) - G''_{37}(1 \text{ rad/sec})}$$ | is not less than 0.5, preferably in the range 0.7 to 3, most preferably in the range 1 to 1.8. |
| | is not less than 0.5, preferably in the range 0.7 to 3, most preferably in the range 1 to 1.8. |

The value of the ratio of $G'_{37}/G''_{37}$ at least for the frequency range above 1 rads/up to 100 rads/s should preferably be not less than 0.5, preferably from 0.7 to 10 and most preferably from 1 to 7.

The rheological behaviour can also be related to the values of the Glass Transition Temperature Tg. For topical adhesives according to the present invention Tg should Particularly preferred polymers are acrylics, sulphonated polymers such as acrylamide sulphonated polymers, vinyl alcohols, vinyl pyrrolidone, polyethylene oxide and mixtures thereof. Most preferred are nitrogen containing polymers.

According to the present invention the 3 dimensional adhesive matrix also essentially comprises a plasticiser, which is preferably a liquid at room temperature. This material is selected such that the polymer may be solubilized or dispersed within the plasticiser. For embodiments wherein irradiation cross linking is to be carried out, the plasticiser must also be irradiation cross linking compatible such that it does not inhibit the irradiation cross linking process of the polymer. The plasticiser may be hydrophilic or hydrophobic.

Suitable plasticisers include water, alcohols, polyhydric alcohols such as glycerol and sorbitol, and glycols and ether glycols such as mono- or diethers of polyalkylene gylcol, mono- or diester polyalkylene glycols, polyethylene glycols (typically up to a molecular weight of about 600), glycolates, glycerol, sorbitan esters, esters of citric and tartaric acid, imidazoline derived amphoteric surfactants, lactams, amides, polyamides, quaternary ammonium compounds, esters such phthalates, adipates, stearates, palmitates, sebacates, or myristates, and combinations thereof. Particularly preferred are polyhydric alcohols, polyethylene glycol (with a molecular weight up to about 600), glycerol, sorbitol, water and mixtures thereof.

Typically the adhesive comprises a ratio of polymer to plasticiser by weight of from 1:100 to 100:1, more preferably from 50:1 to 1:50. However, the exact amounts and ratios of the polymer and plasticiser will depend to a large extent on the exact nature of polymer and plasticisers utilised and can be readily selected by the skilled person in the art. For example a high molecular weight polymer material will require a greater amount of plasticiser than a low molecular weight polymer.

In addition, the adhesive also further preferably comprises a lipid-micellising polymer, i.e. a so-called hypercoiling polymer. This polymer functions to micellise and remove the rolled up pockets of grease from the gel-skin interface.

This hypercoiling polymer has the capability of more effectively solvating the primary surfactant micelles that contact hydrophobic skin contaminant such as skin lipid or skin creme. The consequence of this functional role is that the work of adhesion between adhesive and skin is progressively less affected by the presence of either or both surfactant or hydrophobic skin contaminant.

The hypercoiling polymer preferably comprises any of the following, either alone or in combination: poly (maleic acid styrene), poly (maleic acid butyl vinyl ether), poly (maleic acid propyl vinyl ether), poly (maleic acid ethyl vinyl ether) and poly (acrylic acid ethyl acrylate).

A particularly preferred example is an alternating copolymer of styrene and maleic anhydride. As discussed hereinafter the adhesive seeks to provide a biphasic structure on polymerisation. These two phases are hydrophilic and hydrophobic. The hydrophobic phase may be provided by a hydrophobic monomer which is initially maintained as part of the homogenous reaction mixture by way of a reactive solvent bridge. Alternatively and/or additionally the hydrophobic component is provided as a polymer which separates from the aqueous phase on polymerisation.

The exact amounts and ratios of the hypercoiling polymer will depend to a large extent on the nature of the components.

In certain circumstances the reaction mixture preferably comprises from 3% to 20%, and more preferably from 8% to 18% by weight of the reaction mixture, of a stabilised polymer dispersion that is used to provide a stable phase separated system. The polymer preferably comprises any of the following either alone or in combination: vinylacetate dioctyl maleate copolymer or ethylene-vinyl acetate copolymer. Ethylene-vinylacetate copolymer is preferred, such as that marketed under the trade name DM137 by Harlow Chemicals.

The adhesive also preferably comprise surfactants such as nonionic, cationic, anionic, amphoteric and any mixtures thereof.

Suitable nonreactive nonionic surfactants include but are not limited to those selected from the group consisting of the condensation products of a higher aliphatic alcohol, such as a fatty alcohol, containing about 8 to about 20 carbon atoms, in a straight or branched chain configuration, condensed with about 3 to about 100 moles, preferably about 5 to about 40 moles and most preferably about 5 to about 20 moles of ethylene oxide. Examples of such nonionic ethoxylated fatty alcohol surfactants are the Tergitol.TM. 15-S series from Union Carbide and Brij.TM. surfactants from ICI. Tergitol.TM. 15-S Surfactants include $C_{11}$-$C_{15}$ secondary alcohol polyethyleneglycol ethers. Brij.TM 58 Surfactant is Polyoxyethylene(20) cetyl ether, and Brij.TM.76 Surfactant is Polyoxyethylene(10) stearyl ether.

Other suitable nonreactive nonionic surfactants include but are not limited to those selected from the group consisting of the polyethylene oxide condensates of one mole of alkyl phenol containing from about 6 to 12 carbon atoms in a straight or branched chain configuration, with about 3 to about 100 moles of ethylene oxide. Examples of nonionic surfactants are the Igepal.TM.CO and CA series from Rhone-Poulenc. Igepal.TM.CO surfactants include nonylphenoxy poly(ethyleneoxy) ethanols. Igepal.TM. CA surfactants include octylphenoxy poly(ethyloneoxy) ethanols.

Another group of usable nonreactive nonionic surfactants include but are not limited to those selected from the group consisting of block copolymers of ethylene oxide and propylene oxide or butylene oxide.

Examples of such nonionic block copolymer surfactants are the Pluronic.TM. and Tetronic TM. series of surfactants from BASF. Pluronic.TM. surfactants include ethylene oxide-propylene oxide block copolymers. Tetronic.TM. surfactants include ethylene oxide-propylene oxide block copolymers. Suitable examples are Pluronic L68 and Tetronic 1307. Particularly suitable examples are Pluronic L64 and Tetronic 1107.

Still other satisfactory nonreactive nonionic surfactants include but are not limited to those selected from the group consisting of sorbitan fatty acid esters, polyoxyethylene sorbitan fatty acid esters and polyoxyethylene stearates. Examples of such fatty acid ester nonionic surfactants are the Span.TM., Tween.TM., and Myrj.TM. surfactants from ICI. Span.TM. surfactants include $C_{12}$-$C_{18}$ sorbitan monoesters. Tween.TM. surfactants include poly (ethylene oxide) $C_{12}$-$C_{18}$ sorbitan monoesters. Myrj.TM. surfactants include poly(ethylene oxide) stearates.

Suitable anionic surfactants will normally include a hydrophobic moiety selected from the group consisting of (about $C_6$ to about $C_{20}$) alkyl, alkylaryl, and alkenyl groups and an anionic group selected from the group consisting of sulfate, sulfonate, phophate, polyoxyethylene sulfate, polyoxyethylene sulfonate, polyoxyethylene phosphate and the alkali metal salts, ammonium salts, and tertiary amino salts of such anionic groups.

Anionic surfactants which can be used in the present invention include but are not limited to those selected from the group consisting of (about $C_6$ to about $C_{20}$) alkyl or alkylaryl sulfates or sulfonates such as sodium lauryl sulfate (commercially available as Polystep.TM B-3 from Srepan Co.) and sodium dodecyl benzene sulfonate, (commercially available as Siponate.TM.DS-10 from Rhone-Poulenc); polyoxyethylene (about $C_6$ to about $C_{20}$) alkyl or alkylphenol ether sulfates with the ethylene oxide repeating unit in the surfactant below about 30 units, preferably below about 20 units, most preferably below about 15 units, such as Polystep.TM.B-1 commercially available from Stepan Co. and Alipal.TM.EP110 and 115 from Rhone-Poulenc; (about C.sub.6 to about C.sub.20) alkyl or alkylphenoxy poly(ethyleneoxy)ethyl mono-esters and di-esters of phosphoric acid and its salts, with the ethylene oxide repeating unit in the surfactant below about 30 units, preferably below about 20 units, most preferably below about 15 units, such as Gafac.TM.RE-510 and Gafac.TM.RE-610 from GAF.

Cationic surfactants useful in the present invention include but are not limited to those selected from the group consisting of quaternary ammonium salts in which at least one higher molecular weight group and two or three lower molecular weight groups are linked to a common nitrogen atom to produce a cation, and wherein the electrically-balancing anion is selected from the group consisting of a halide (bromide, chloride, etc.), acetate, nitrite, and lower alkosulfate (methosulfate etc.). The higher molecular weight substituent(s) on the nitrogen is/are often (a) higher alkyl group(s), containing about 10 to about 20 carbon atoms, and the lower molecular weight substituents may be lower alkyl of about 1 to about 4 carbon atoms, such as methyl or ethyl, which may be substituted, as with hydroxy, in some instances. One ore more of the substituents may include an aryl moiety or may be replaced by an aryl, such as benzyl or phenyl.

In a particularly preferred embodiment of the invention the surfactant comprises at least one propylene oxide/ethylene oxide block copolymer, for example such as that supplied by BASF Plc under the trade name Pluronic L64. The reaction mixture ideally comprises form 0.1% to 5%, by weight of the reaction mixture, of surfactant.

The surfactant acts to remove the grease from the skin and to form the removed grease into isolated pockets within the hydrogel without reducing the work of adhesion of the coating.

Other common additives known in the art such as preservatives, antioxidants, pigments, mineral fillers and mixtures thereof may also be comprised within the adhesive composition in quantities up to 10% by weight each respectively.

According to the present invention the polymer component of the adhesive can be physically or chemically cross-linked in order to form the 3 dimensional matrix. Physical cross linking refers to polymers having cross links which are not chemical covalent bonds but are of a physical nature such that there are areas in the 3 dimensional matrix having high crystallinity or areas having a high glass transition temperature. Chemical cross-linking refers to polymers which are linked by chemical bonds. Preferably the polymer is chemically cross-linked by radiation techniques such as thermal-, E beam-, UV-, gamma or micro-wave radiation.

In addition when chemical crosslinks are formed in the system, a polyfunctional cross linker and/or a free radical initiator may be present in the premix to initiate the crosslinking upon irradiation. Such an initiator can be present in quantities up to 5% by weight, preferably from 0.02% to 2%, more preferably from 0.02% to 0.2%. Suitable photoinitiators include type I-α-hydroxy-betones and benzilidimethyl-betols e.g. Irgocure 651 which are believed to on irradiation to form benzoyl radicals that initiate polymerization. Particularly preferred is I-hydroxycyclohexylphenylketone (available under the trade name Irgacure 184 from Ciba Speciality Chemicals). In addition from 0.02% to 2% of thermal initiators may also be used.

The resulting adhesive composition is mainly hydrophilic. Hydrophobic and mixed phase compositions are dependant upon the nature of the components of the adhesive. In addition a mixture of monomers whether hydrophilic or both hydrophilic and hydrophobic may result in a single phase or mixed phase of at least 2 phases. Preferably, the adhesives of the present invention are mixed phase hydrophilic hydrophobic.

A mixture of monomers which may result in 1, 2 or more phases are preferred. Mixed phase adhesives are compositions in which both hydrophobic and hydrophilic components, preferably in both plasticisers and polymers, form two or more separate phases. In such cases an emulsifier is preferably present at a suitable level to form stable emulsions between the incompatible phases.

Whilst not intending to be bound by theory it is believed that the improved peel strength liquid stability particularly with respect to water of the adhesives is obtained from a monomer mix comprising both hydrophilic e.g. polar and/or ionic monomers preferably an ionic water soluble monomer and hydrophobic i.e nonionic monomers. Preferably the ratio of hydrophilic monomers to hydrophobic monomers should be in the range of from 5:1 to 1:5, preferably from 3:1 to 1:3, more preferably from 2:1 to 1:2. The hydrophilicity and hydrophobicity of a monomer component is always relative to the other component. Typically prior art hydrogel adhesives comprise hydrophilic monomers only, as a consequence of which they have a high rate of water absorption and do not maintain adhesion after exposure to excess liquid. Whilst not intending to be bound by theory, it is believed that the presence of a hydrophobic component in the adhesive matrix reduces the rate of absorption of water of the adhesive. As a result the distribution of the water absorbed by the adhesive is more uniform. Consequently a water film is not generated between the surface of the skin and the adhesive, which if present, prevents the formation of bonds between skin and adhesive and thus the adhesive capacity of the adhesive itself.

Thus the invention seeks to provide a homogeneously dispersed reaction mixture comprising both hydrophobic and hydrophilic components which, on polymerisation separates into a biphasic or a multiphasic structure. The phases have in some cases been observed to have a thickness of about 100 microns +/−50 microns. The reaction mixture may contain one or more surface active agents which may assist or promote phase separation but in the course of polymersation become anistropically distributed between the result phases.

The presence of a hydrophobic monomer or polymer may be necessary in the initial homogenous dispersion in order to more effectively promote phase separation.

It is a consequence of this invention that the phase separated material contains relatively hydrophobic regions, which enable the polymer to function as a pressure sensitive adhesive, and substantially hydrophilic region, which enable the surface active agent to function in an aqueous environment at the interface between the polymer and mammalian skin. When the polymer is placed in contact with skin, the nature and quantity or surface active agent are chosen to bring about the removal of natural or synthetic hydrophobic material, such as skin lipid or skin creme, from the skin surface without adversely diminishing the work of adhesion between the hydrophobic domains and the skin surface. In as much as both the polymeric adhesive formed in this invention and the skin with which it is contacted are deformable under conditions of normal use, an equilibrium interfacial situation is reached in which some spatial exchange of hydrophobic regions and hydrophobic regions will have taken place on the skin surface.

Suitable preferred hydrophilic monomers are acrylic acid, and salts thereof, 2-acrylamido methylpropane sulphonic acid, acrylic (3-sulphopropyl) ester acid and salts thereof and combinations thereof. Suitable hydrophobic monomer components are acrylamide, acrylonitrile, methyl-, ethyl-, butyl hexyl, iso octyl- and isodecyl acrylates and methacrylate, vinyl ethers, vinyl pyrrolidine, gylcidyl acrylate and 2-hydroxyethyl acrylate, tehra-hydrofurfuryl acrylate, hydroxypropyl acrylate, vinyl propionate and vinyl butyrate, and combinations thereof. Particularly preferred are ethoxy ethyl acrylate or butyl acrylate.

When the adhesive comprises a hydrophobic component, such as butyl acrylate as well as a hydrophilic monomer (i.e. the aforesaid water soluble ionic monomer), such as NaAMPS, the nonionic water soluble monomer, for example NNDMA, acts as a so-called "reactive solvent bridge" to provide intimate mixing of the various seemingly incompatible components of the reaction mixture prior to polymerisation. The reaction mixture thus has a homogenous structure containing both hydrophilic and hydrophobic components that are intimately mixed, as the NNDMA acts as a solvent for both hydrophilic and hydrophobic materials, providing a clear compatible coating solution or dispersion. As the reactive solvent bridge is polymerised and thus essentially removed from the reaction mixture the stability of the system is adversely affected and the compatible coating solutions or dispersions undergo phase separation so as to provide a biphasic structure.

In preparing adhesive compositions in accordance with the invention, the ingredients will usually be mixed to provide a reaction mixture in the form of an initial pre-gel aqueous based liquid formulation, and this is then converted into a gel by a free radical polymerisation reaction. This may be achieved for example using conventional thermal initiators and/or photoinitiators or by ionizing radiation. Photoinitiation is a preferred method and will usually be applied by subjecting the pre-gel reaction mixture containing an appropriate photoinitiation agent to UV light after it has been spread or coated as a layer on siliconised release paper or other solid substrate. The incident UV intensity, at a wavelength in the range from 240 to 420 nm, is ideally substantially 40 mW/cm². The processing will generally be carried out in a controlled manner involving a precise predetermined sequence of mixing and thermal treatment or history.

The UV irradiation time scale should ideally be less than 60 seconds, and preferably less than 10 seconds to form a gel with better than 95% conversion of the monomers and for conversion better than 99.95% exposure to UV light less than 60 seconds and preferably less than 40 seconds is preferred. Those skilled in the art will appreciate that the extent of irradiation will be dependent on the thickness of the reaction mixture, concentration of photoinitiator and nature of substrate on to which the reaction mixture is coated and the source of UV.

These timings are for medium pressure mercury arc lamps as the source of UV operating at 100 W/cm. The intensity of UV@254 nm and 313 nm reaching the surface of the substrate is approximately 150 $\mu$W/cm² and 750 $\mu$W/cm². For a given lamp UV intensity in a function of the operating power and distance of the reaction mixture from the UV source.

In order to minimize and preferably eliminate the presence of any residual monomers it is important to ensure that the reaction is complete. This is dependent upon a number of factors such as the substrate onto which the adhesive is applied, the type and intensity of the ultra violet light and the number of ultra violet light passes. Preferably the conversion of the hydrophilic monomers present such as NaAMPS should be 98%, preferably 99.0% most preferably 99.9% so that the amount of monomer within the adhesive is 4600 microg/g or less, preferably 2300 microg/g or less, most preferably 230 microg/g or less. Similarly, the conversion of the hydrophobic monomers present such as NNDMA should be 99%, preferably 99.9%, most preferably 99.99% so that the amount of monomer present in the adhesive is 2200 microg/g or less, preferably 220 microg/g or less, most preferably 22 microg/g or less.

The adhesive is thus typically formed by polymerising an aqueous reaction comprising from 5 to 50%, preferably form 30% to 50% by weight of the reaction mixture, of hydrophilic monomer, i.e. an ionic water soluble monomer, from 10% to 50%, preferably from 15% to 45% by weight of the reaction mixture, of a plasticiser (other than water), from 10% to 50%, preferably from 15% to 30% more preferably from 15% to 25% by weight of the reaction mixture, of a hydrophobic nonionic monomer, i.e. nonionic water soluble monomer, from 3 to 40%, by weight of the reaction mixture, of water. If present the reaction mixture comprises from to 10%, by weight of the reaction mixture, of a surfactant. Similarly the reaction mixture may also comprise from 0.1% to 5%, by weight of the reaction mixture, of a lipid micelling polymer.

The adhesive is provided, typically on at least a portion of the wearer facing surface of the flange, as a layer having a thickness or calliper C that is preferably constant, or that alternatively can vary over the surface of application of the adhesive.

When considering particularly the removal phase of an adhesive composition for attachment to the skin of a wearer, it is commonly recognised that good conditions of removal, i.e. at a frequency of about 100 rad/sec, of the adhesive applied to at least part of the wearer facing surface of the flange, are achieved when the adhesive can be easily removed from the skin, and particularly from the bodily hair that may be located on this area of the skin, where the flange contacts the body, without causing pain to the wearer, therefore without adhering too hard upon removal, to the skin and the hair of the wearer. Moreover, a good removal implies that the adhesive does not leave residues on the skin or on the hair.

The relationship between the thickness or calliper C measured in millimeters (mm) of the layer of the adhesive typically onto at least part of the wearer's facing surface of the flange of the disposable human waste management device, and the viscous modulus $G''_{25}$ at 25° C. at about 100 rad/sec of the topical adhesive gives an indication of painless and easy removal of the adhesive from the skin.

Without being bound to any theory, it is believed that for higher values of $G''_{25}$ at 100 rad/sec, which overall correspond to a higher adhesiveness of the composition, a thicker calliper or thickness C of the adhesive layer is needed so that the energy applied for the removal is more evenly distributed within the mass of the adhesive, and is therefore transferred smoothly to the skin, so avoiding peaks of energy that typically cause the pain sensation to the wearer. In other words, thinner layers of the adhesive necessitate an adhesive with a lower $G''_{25}$ at 100 rad/sec to achieve a reduced pain sensation upon removal of the device.

According to the present invention, the adhesive is preferably provided as a layer having a thickness C such that the viscous modulus $G''_{25}$ (100 rad/sec) and the thickness C of the adhesive layer satisfy the following empirical equation:

$$G''_{25} \leq [(7.00+C) \times 3000] Pa$$

and preferably the following empirical equation:

$$G''_{25} \leq [(5.50+C) \times 1700] Pa$$

While in a preferred embodiment of the present invention the thickness C of the adhesive layer is constant, such an adhesive layer can also have different thicknesses in different portions of the wearer facing surface of the flange where it is applied, provided that the above mentioned relationship between C and $G''_{25}$ is in any case satisfied in each portion.

According to the present invention any disposable human waste management device known in the art can be provided with the adhesive according to the present invention as defined herein.

Typically urine or faecal management devices (10) comprise a bag (11) having an aperture (21) and a flange (12) surrounding the aperture for preferably adhesive attachment to the uro genital area and or the perianal area of a wearer as visible from FIGS. 1 and 4. Any faecal or urine management device known in the art can be provided with an adhesive according to the present invention.

The bag (11) as used herein is a flexible receptacle for the containment of urine and excreted faecal matter. The bag (11) can be provided in any shape or size depending on the intended use thereof, i.e. whether the device is intended for bedridden patients or active patients suffering from incontinence or requiring an artificial bowel or for infants. For example, elongated bags which are principally tubular or rectangular are typically utilised by bedridden patients and elderly incontinence sufferers. For more active wearers whether infants or adults, the disposal human waste management device should preferably be anatomically shaped such that the device follows the contours of the body and can be worn inconspicuously by the wearer under normal garments.

Particularly, preferred shapes are flat circular type bags, cone shaped bags, truncated shaped bags and pyramidal or truncated pyramidal shaped bags. In a most preferred embodiment of a faecal management device of the present invention, the bag (11) has a substantially truncated cone shape. A preferred shape bag for urine devices is shown in FIG. 4. Typically the bags will have a wearer facing portion (16) and a garment facing portion (17). The wearer facing portion (16) of the faecal management device (10) is disposed adjacent the buttocks of the wearer. As such, the wearer facing portion (16) amply covers the buttocks of the wearer and does not hang between the thighs of the wearer.

In addition, the bag (11) is preferably shaped to allow at least partial insertion and retention of the bag in-between the buttocks of the wearer and thereby ensure good contact between the flange and the skin of the wearer. For example, the bag (11) may be provided with a neck portion or conduit.

The bag (11) is preferably designed to provide sufficient volume for urine and/or faecal material under a variety of wearing conditions, also when worn by a freely moving, i.e. not bedridden wearer. Sitting on the bag, for example, will result in a largely reduced volume in some areas of the bag. Thus, the bag (11) is preferably shaped to provide sufficient volume in areas which are not subjected to much pressure in wearing conditions such as sitting.

The bag (11) is designed to safely contain any entrapped material, typically it will be liquid impermeable, yet it may be breathable. The bag (11) is designed of sufficient strength to withstand rupture in use, also when pressure on the bag (11) is exerted in typical wearing conditions, such as sitting.

According to the present invention, depending on the shape of the bag (11) required, the bag (11) may be provided from a unitary piece of material or from a number of separate pieces of material, which may be identical or different and which are sealed at their respective peripheries.

In one preferred embodiment the bags herein have a wearer facing portion (16) and a garment facing portion (17) which comprise separate pieces of material. The wearer facing portion (16) and the garment facing portion (17) are sealed at the periphery of the bag (11), thus creating a bag peripheral rim (18). As is visible from FIG. 1, the wearer facing portion (16) of the bag (11) may comprise two further sections (19), which are secured to each other by means known to the man skilled in the art, such as adhesive, thermobonding or pressure bonding in order to provide the desired bag configuration. Said rim (18) may also be inside the bag, thus being coextensive with the inner surface (15) of the bag (11) rather than with the outer surface (30) of the bag (11). Preferably the bag (11) is asymmetrical to the transversal axis, so that the distance measured in the longitudinal direction from the centre of the aperture (21) to the front end of the bag (11) is shorter than the distance measured to the rear end of the bag (11).

According to the present invention the bag (11) can comprise one or multiple layers, preferably two or three layers. The layer on the inside of the bag (11), which will typically at least partially come in contact with faecal material is called the inner layer. The outermost layer of the bag, which will typically at least partially come in contact with the skin to the wearer and the garments of the wearer, is called the outer layer.

The layers of the bag material may be provided from any material, preferably so that the bag is liquid impervious. The layers may in particular comprise any material such as non-wovens or films. In a preferred embodiment of the present invention a laminate may be formed from a non-woven layer and a film. The laminate can be formed by means known to the man skilled in the art.

Any non-woven layer can comprise felt fabrics, spunlaced fabrics, fluid jet entangled fabrics, air-laid fabrics, wet-laid fabrics, dry-laid fabrics, melt-blown fabrics, staple fibre carding fabrics, spunbonded fabrics, stitch-bonded fabrics, apertured fabrics, combinations of the above or the like.

Suitable film materials for any of said layers preferably comprise a thermoplastic material. The thermoplastic material can be selected from among all types of hot-melt adhesives, polyolefins especially polyethylene, polypropylene, amorphous polyolefins, and the like; material containing meltable components comprising fibres or polymeric binders including natural fibres such as cellulose—wood pulp, cotton, jute, hemp; synthetic fibres such as fibreglass, rayon, polyester, polyolefin, acrylic, polyamid, aramid, polytetrafluroethylene metal, polyimide; binders such as bicomponent high melt/low melt polymer, copolymer polyester, polyvinyl chloride, polyvinyl acetate/chloride copolymer, copolymer polyamide, materials comprising blends wherein some of the constituent materials are not meltable; air and vapour permeable materials including microporous films such as those supplied by EXXON Chemical Co., III, US under the designation EXXAIRE or those supplied by Mitsui Toatsu Co., Japan under the designation ESPOIR NO; and monolithic breathable materials such as Hytrel™ available from DuPont and Pebax™ available from ELF Atochem, France.

In a preferred embodiment a film, which is comprised in any layer, is preferably permeable to gases such as air and to vapour such as water vapour in order to avoid the problem of entrapment and condensation of moisture vapour given off by the body of the wearer and thus, the hot, clammy and uncomfortable conditions after a short period of use.

The outer layer of the bag is preferably provided with a non-woven layer. Such material layers present an uneven surface to the skin of the wearer and thus reduce significantly the problem of occlusion and greatly improve skin healthiness.

In one preferred embodiment of the present invention the bag comprises two layers. Preferably the outer layer comprises a non-woven layer and the inner layer comprises a film.

In yet another preferred embodiment of the present invention, the bag (11) comprises three layers, preferably one film and two non-woven layers. In an even more preferable embodiment the film is interposed between the two non-woven layers. This sequence of layers results in a closed fibrous structure, which has a particularly pleasing sensation on contact with the skin of the wearer. In yet another preferred embodiment the inner layer comprises a film and the other two layers comprise non-wovens.

The non-woven layer or the non-woven layers comprised by the bag (11) may be hydrophobic or hydrophilic. If the bag (11) does not comprise a film layer, preferably at least one non-woven layer is hydrophobic. As a consequence, fluid penetration is resisted through the wearer facing portion (16) and the garment facing portion (17) of the faecal management device (10). If the bag comprises a film or a hydrophobic non-woven layer, further non-woven layers may be hydrophilic.

Typically, the non-woven layer is treated with a surface active material, such as a fluorchemical or other hydrophobic finishings, to provide the requisite hydrophobicity. The non-woven layer, however, may equally be treated with coatings of liquid impervious materials such as hot-melt adhesives or coatings of silicone or other hydrophobic compounds such as rubbers and vegetable and mineral waxes or it may be physically treated using nano-particulates or plasma coating techniques, for example.

The non-woven layer can also be treated with agents to improve the tactile perceivable softness of the wearer facing portion (16) and the garment facing portion (17). The agents include but are not limited to vegetable, animal or synthetic oils, silicone oils and the like. The presence of these agents are known to impart a silky or flannel-like feel to the non-woven layer without rendering it greasy or oily to the tactile sense of the wearer. Additionally, surfactant material, including anionic, nonionic, cationic and amphotene surfactants, may be added to further enhance softness and surface smoothness.

Furthermore, the non-woven layer may be impregnated with a lotion to provide desirable therapeutic or protective coating lotion benefits. The lotion coating on the wearer facing portion (16) and the garment facing portion (17) is transferable to the skin of the wearer by normal contact and wearer motion and/or body heat. Generally, mineral oil in the form of a lotion is recognised as being effective in imparting a soothing, protective coating to the skin of the wearer. It is also possible to impregnate the non-woven layer with a solid oil phase of cream formulation or to incorporate into the non-woven layer an array of pressure- or thermal- or hydrorupturable capsules containing for example, baby oil.

In one embodiment of the present invention the bag (11) may contain absorbent material. The absorbent material may comprise any absorbent material which is capable of absorbing and retaining liquids. The absorbent material may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The absorbent material may be positioned in the bag (11) in any suitable manner. For example, the absorbent material may be loosely arranged within the bag or may be secured to the inner layer of the bag (11). Any known techniques for securing absorbent material to nonwoven and film substrates may be used to secure the absorbent material to the inner layer of the bag. The absorbent material may also be arranged to have any desired shape or configuration (e.g., rectangular, oval, circular, etc.).

In the embodiment shown in FIG. 4, the outer surface of bag (11) is provided with patches of adhesive (40) for securing the bag (11) to the body of the wearer. Preferably, the patches of adhesive (40) are positioned on the outer surface of bag (11) such that they are secured to the abdomen of the wearer in use. Any number, size and shape of adhesive patches (40) may be used depending on the intended use of the device.

The human waste management device in particular urine management devices according to the present invention also preferably comprise an additional acquisition layer. The acquisition layer is typically secured to the inner surface of bag. However, the acquisition layer may also be secured to the flange, or both the flange and the inner surface of bag. The acquisition layer is preferably positioned such that it separates the genitalia of the wearer from coming into direct contact with the absorbent material. The acquisition layer is fluid pervious allowing urine to readily pass through so that it may be absorbed by absorbent material.

The acquisition layer may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. If the acquisition, barrier layer includes fibers, the fibers may be spunbond, carded, wet-laid, meltblown, hydroentangled, or otherwise processed as is known in the art.

The acquisition layer is designed to have a pore size such that the absorbent material is not allowed to pass through and contact the wearer's skin. While designed not to have to large of a pore size which permits the passage of absorbent material, the acquisition layer preferably has a pore size which is greater than the pore size of the absorbent material.

Preferably, the acquisition layer is less hydrophilic than the absorbent material. The acquisition layer may be treated with a surfactant to increase its initial wettability. When treated with surfactant, however, the acquisition layer should still be less hydrophilic than the absorbent material. Suitable methods for treating the acquisition layer with a surfactant include spraying the acquisition layer with the surfactant and immersing the material into the surfactant. Alternatively, a surfactant may be incorporated into the acquisition layer.

As shown in FIG. 1 the bag (11) is provided with an aperture (21) whereby excreted matter is received from the body prior to storage within the bag cavity. The aperture (21) is surrounded by a flange (12) and may be provided in any shape or size, such as circular, oblong, heart shaped and may be symmetrical or asymmetrical, preferably the aperture has an oblong configuration either in the longitudinal or in the transversal direction or in both directions, e.g. the contours of the aperture are in the shape of two ellipses with the respective main axes being substantially perpendicular.

The flange (12) is attached to the bag (11) according to any means known to the man skilled in the art which may provide permanent or releasable attachment. Preferably however, the flange is attached to the bag by adhesive. Typically, the bag will be attached to the flange, towards the outer periphery of flange so as not to cause any obstruction for the entering matter.

The flange may be provided in any size depending on the wearer group for which the device is intended. Similarly the flange may be provided in any shape and preferably has a symmetrical shape preferably comprising a plurality of lobes (13). The flange (12) may comprise a front projection (28) and a rear projection (29) to the perineal and coccygeal area of a wearer.

The flange comprises a garment facing surface (22) and a wearer facing surface (23). In an preferred embodiment these are two large, substantially flat surfaces, however, the flange may also comprise projections designed to fit the perineal or coccygeal area of the wearer.

The flange (12) should be made of soft, flexible and malleable material to allow easy placement of the flange to the perianal area. Typical materials include nonwoven materials, wovens, open celled thermoplastic foams, closed-cell thermoplastic foams, composites of open celled foams and stretch nonwoven, and films. A closed-cell foam of polyethylene has been found effective, but more preferably an open celled polyurethane foam is used. Preferably, such foams have a thickness within the general range of 0.1 to 5 millimeters and a density of 5 to 250 $g/m^2$, more preferably 50 $g/m^2$. Other thermoplastic foam materials, or other suitable plastics sheet materials having the described properties of such foams (i.e., softness, pliability, stretchability, and contractability) might also be used. Preferably, the material of garment facing surface (23) of the flange (12) may extend into the defined aperture area so as to form a skirt or flap of material which prevents unintentional adhesion of the surface edges of the flange defining the aperture to oneanother during use.

According to the present invention the adhesive (20) is preferably covered with a release means (not shown) in order to protect the adhesive (20), such as siliconized paper. The adhesive (20) can cover the entire wearer facing surface (23) of the flange (12) or more preferably have at least one, preferably two to six non-adhesive portions. These portions may be adhesive free or may contain inactivated or covered adhesives. As is evident from FIG. 1, the adhesive is in one preferred embodiment not applied to the entire wearer facing surface area of the flange (12), so as to provide lobes (13) on either side of the flange (12) which are non-adhesive and can thereby serve to facilitate placement and removal of the device whilst avoiding contact with the adhesive. These lobes are however preferably also covered by the release means. Before application of the faecal management device (10) to the skin of the wearer, the release means if present is removed.

The adhesive (20) can be applied to the wearer facing surface of the flange (12) by any means known in the art such as slot coating, spiral, or bead application or printing. Typically the adhesive is applied at a basis weight of from 20 $g/m^2$ to 2500 $g/m^2$, more preferably from 500 $g/m^2$ to 2000 $g/m^2$ most preferably from 700 $g/m^2$ to 1500 $g/m^2$ depending on the end use envisioned. For example, for faecal management devices (10) to be used for babies the amount of adhesive may be less than for faecal management devices (10) designed for active adult incontinence sufferers.

Figure 2:
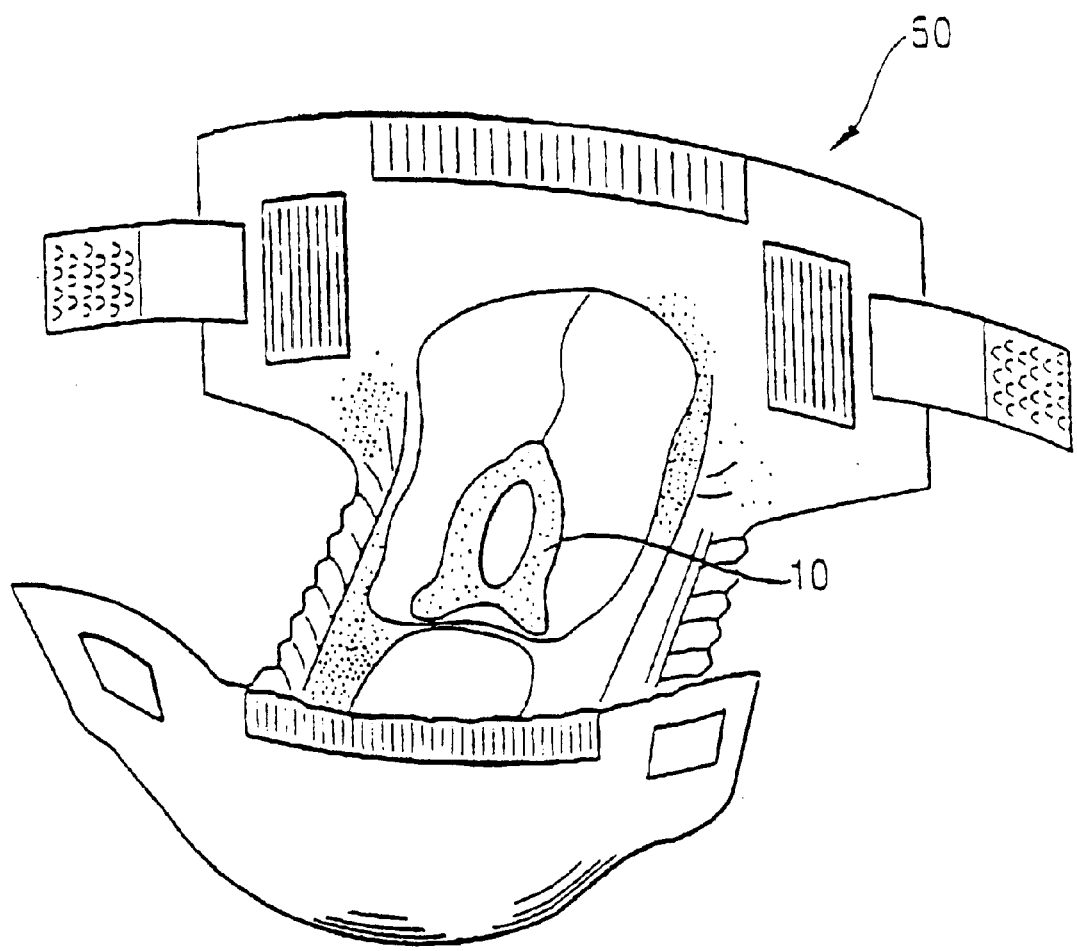
FIG. 2 shows a perspective view of the disposable faecal management device in conjunction with a disposable diaper.

The disposable human waste management device (10) of the present invention has been found to be particularly useful and beneficial when used in conjunction with a garment, or diaper (50), preferably a disposable diaper—refer to FIG. 2. The disposable human waste management device (10) is preferably first positioned in the perianal area of the wearer before the disposable diaper (50) is applied. In particular, the diaper (50) is positioned over the disposable human waste management device (10) and fastened in a conventional manner around the body of the wearer. It has been found that, in addition, to providing excellent separation between urine and faecal material, the combined disposable human waste management device (10) and diaper (50) system actually reduces skin irritation, which may at times occur, especially since the group of typical wearers includes the very old, the very young and the unhealthy wearers. In effect, the presence of the disposable human waste management device (10) permits the formation of a separation layer between the skin of the wearer and the diaper (50), i.e. a part of the absorbent core (58) of the diaper (10). The diaper (50) can be of the conventional type (an embodiment of which is described below although not a limiting example by any means) or can be adapted to contain in an effective and comfortable manner the disposal human waste management device (10) according to the teachings of the present invention.

As used herein, the term "disposable diapers" refers to articles which absorb and contain body extrudates; and more specifically, refers to articles which are placed against or in proximity to the body of the wearer to absorb and contain the various extrudates discharged from the body and which are intended to be discarded after a single use (i.e., they are not intended to be laundered or otherwise restored or reused) and, preferably, to be recycled, composted or otherwise disposed of in an environmentally compatible manner. As used herein, the term "diaper" refers to a garment generally worn by infants or incontinence sufferers that is drawn up between the legs and fastened about the waist of the wearer.

Figure 3:
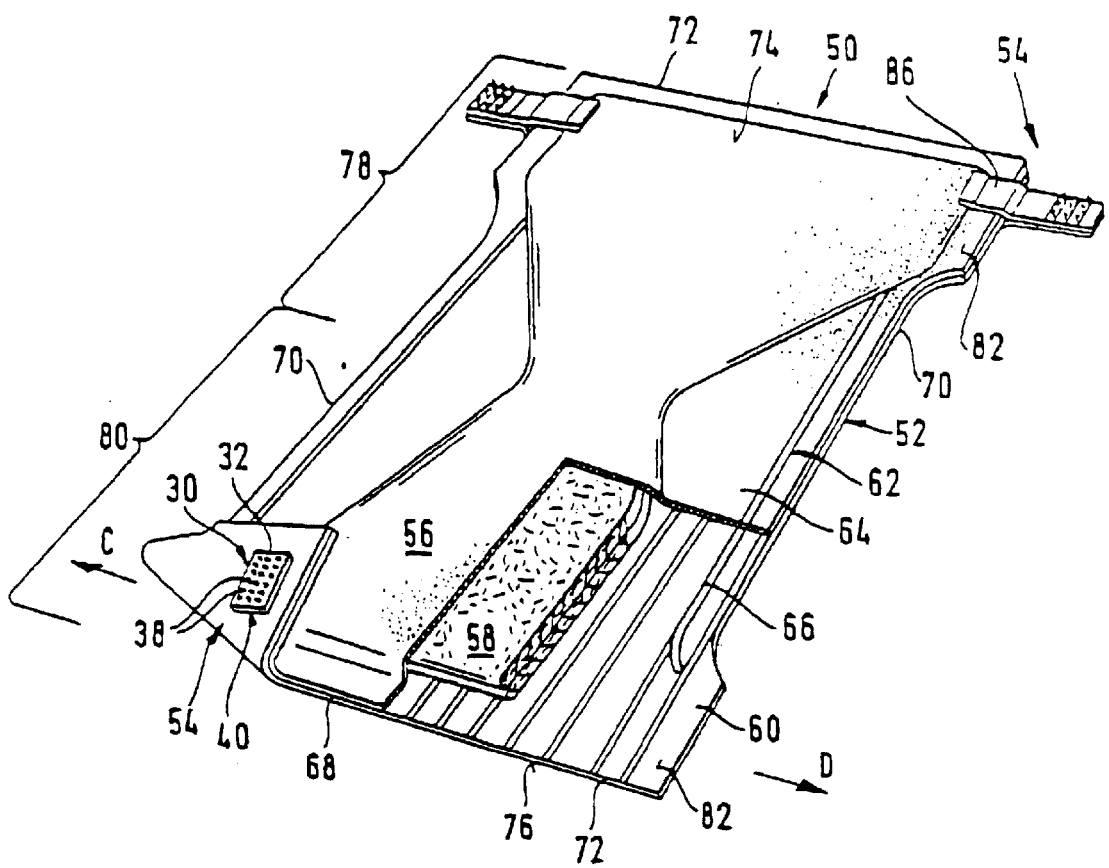
FIG. 3 is a partially cut-away perspective view of a disposable diaper embodying a faecal management device of the present invention.

FIG. 3 is a partially cut-away perspective view of a diaper (50) embodying the present invention prior to it being placed on the wearer over the faecal management device (10). As is visible from FIG. 3, a preferred diaper (50) comprises a body portion (52) and a refastenable mechanical fastening device (54). A preferred body portion (52) comprises a liquid pervious topsheet (56), and absorbent core (58), a liquid impervious backsheet (60), and elastically contractible leg cuffs (62); each leg cuff (62) preferably comprising a side flap (64) and one or more elastic members (66). For simplicity purposes, only one elastic member (66) is shown in the side flap (64). While the topsheet (56), the absorbent core (58), the backsheet (60), the side flaps (64), and the elastic members (66) may be assembled in a variety of well-known configurations. A preferred disposable diaper configuration is shown and generally described in U.S. Pat. No. 3,860,003, an even more preferred disposable diaper configuration is shown and generally described in WO 93/16669. In this preferred diaper configuration, the backsheet (60) is joined to the topsheet (56); the absorbent core (58) is positioned between the topsheet (56) and the backsheet (60); the side flaps (64) extend outwardly from and along each side edge of the absorbent core (58); and the elastic member (66) is operatively associated with each side flap (64).

FIG. 3 shows the body portion (52) in which the topsheet (56) and the backsheet (60) are coextensive and have length and width dimensions generally larger than those of the absorbent core (58). The topsheet (56) is superposed on the backsheet (60) thereby forming the periphery (68) of the body portion (52).

The body portion (52) has an inside surface (74) and an outside surface (76). When a backsheet (60) is used, it typically forms the outside surface (76) of the body portion (52). The inside surface (74) is that surface of the diaper (50) opposite the outside surface (76) and in the embodiment shown is typically formed by the topsheet (56). In general, the inside surface (74) of the diaper (50) is that surface coextensive with the outside surface (76) and which is for the greater part in contact with the wearer when the diaper (50) is worn.

The absorbent core (58) of the body portion (52) may be any absorbent means which is generally compressible, conformable, non-irritating to the skin of the wearer, and capable of absorbing and retaining liquids such as urine and other certain bodily discharges. The absorbent core (58) may be manufactured in a variety of sizes and shapes (for example, rectangular, hour-glass, "T"-shaped, asymmetric, etc.) and from a wide variety of liquid absorbent materials commonly used in disposable diapers and other absorbent articles such as comminuted wood pulp which is generally referred to as airfelt. Examples of other suitable absorbent materials include creped cellulose wadding, meltblown polymers including coform, crosslinked cellulosic fibers, tissue including tissue wraps, absorbent foams, absorbent sponges, superabsorbent polymers, absorbent gelling materials, or any equivalent materials or combinations of materials. The configuration and construction of the absorbent core (58) may also be varied (for example, the absorbent core (58) may have varying calliper zones, hydrophilic gradients, superabsorbent gradients, or lower average density and lower average basis weight acquisition zones; or may comprise one or more layers or structures). Further, the size and absorbent capacity of the absorbent core (58) may be varied to accommodate wearers ranging from infants to adults.

The backsheet (60) is impervious to liquids (for example, urine) and is preferably manufactured from a thin plastic film, preferably a thermoplastic film, although other flexible liquid impervious materials may also be used. As used herein, the term "flexible" refers to materials which are compliant and which will readily conform to the general shape and contours of the human body. The backsheet (60) prevents the exudates absorbed and contained in the absorbent core (58) from soiling articles which are in contact with the diaper (50) such as undergarments and bedding. The backsheet (60) may thus comprise polymeric films such as thermoplastic films of polyethylene or polypropylene, or composite materials such as film-coated non-woven material. Exemplary films are manufactured by Tredegar Industries, Inc. of Terre Haute, Ind., USA or BP-Chemical PlasTec, Rotbuchenstrasse 1, D-8000 München, Germany.

The backsheet (60) is preferably textured to provide a more clothlike appearance. Further, the backsheet (60) may also permit vapours to escape from the absorbent core (58) while still preventing exudates from passing through the backsheet (60) by, for example, being supplied with microapertures. The size of the backsheet (60) is dictated by the size of the absorbent core (58) and the exact diaper design selected.

The topsheet (56) of the diaper is compliant, soft feeling and non-irritating to the skin of the wearer. Further, the topsheet (56) is liquid pervious permitting liquids (for example, urine) to readily penetrate through its thickness. A suitable topsheet (56) may be manufactured from a wide range of materials, such as porous foams, reticulated foams, apertured films; or woven or non-woven webs of natural fibres (for example, wood or cotton fibres) or from a combination of natural and synthetic fibres. Preferably, it is made of a material that isolates the skin of the wearer from liquids retained in the absorbent core (58).

There are a number of manufacturing techniques which may be used to manufacture the topsheet (56). For example, the topsheet (56) may be a non-woven web of fibres. An exemplary topsheet (56) is carded and thermally bonded by means well-known to those skilled in the fabric art. A suitable topsheet (56) is manufactured by, for example, Veratec Inc., a division of International Paper Company, of Walpole, Mass., USA. A topsheet (56) particularly preferred for incontinence garments comprises a formed thermoplastic film.

Test Methods
Peel adhesion method

This is a quantitative method to determine the average peel force required to remove a skin at a specified peel angle and speed.

Equipment

| | |
|---|---|
| Scissors | Convenient source |
| Standard ruler | Convenient source |
| Steel Roller | 5.0 kg Mass. 13 cm in diameter and 4.5 cm in width covered with 0.5 mm thick rubber. |
| Polyester Film | PET 23μ available from EFFEGIDI S.p.A., 43052 Colorno, Italy. |
| Transfer Adhesive | 3M 1524 available from 3M Italia S.p.a., 20090 Segrate Italy |
| Stop watch | Convenient source |
| Tensile Tester | Instron mod.: 6021 (or equivalent) |

Test procedure

A) Tensile Tester Peel Settings:

| | |
|---|---|
| Load cell | 10 N |
| Test Speed | 1000 mm/min |
| Clamp to Clamp distance | 25 mm |
| Pre Loading | 0.2 N |
| Test Path "LM" | 50 mm |
| Measure variable | F average (N) in "LM" |

B) Skin Condition and Preparation

The sample is peel from the forearm. There are 3 conditions of the skin that are tested:
1) Dry: The forearm is untreated and not wiped prior to test or between repetitions.
2) Wet: To one cotton disk (Demak'up diameter 5.5 cm, weight about 0.6 g), 3 ml of distilled water is added. Next the disk is then wiped with a light pressure 3 times over the test area on the forearm. (The test area of the forearm is a rectangle approximately 2 cm wider and longer than the adhesive area).
3) Greasy: To one cotton disk (Demak'up diameter 5.5 cm, weight about 0.6 g), 4 drops (about 0.2 g) of 'Nivea Body' are added. The disk is then folded in on itself to ensure the cream is absorbed. Next the disk is then wiped with a light pressure 3 times over the test area on the forearm. (The test area of the forearm is a rectangle approximately 2 cm wider and longer than the adhesive area).

C) Sample Preparation
1. Allow the samples to adjust to conditioned room (23±2° Celsius and 50±2%RH) for about 1 hr.
2. Prepare rectangular adhesive samples 260 mm±2 length and 20 mm±2 wide.
3. Attach on the sample surface the polyester film (using the transfer adhesive to attach the polyester to the substrate surface).

4. Each test specimen should be prepared individually and tested immediately.
5. Remove the release paper from the adhesive without touching it. Attach one end to the skin (see section B).
6. Roll the Steel Roller for 160 mm along the adhesive strip, once in each direction.

D) Test Environment

There are 2 environments the adhesive can be tested in:
1) Conditioned Room as described in C1.
2) Wet Environment. Here, after step C4, the specimen is taken and put in a humidity controlled oven for 3 hours at 85 deg C. It is then taken out and steps C5, C6 are carried out.

E) Execution 1 minute after Step C6, take the free end of the specimen (approx. 100 mm long) and insert it in the upper end of the adhesion testing machine. Ensure the specimen is at a 90 degree angle to the forearm. Start the testing machine.

F) Report

Report the average of the peel strength of 5 tests. The single values are the base to calculate the standard deviation between the samples.

Residual Monomer Test Method

Test Sample 1 gram of a hydrogel sample is taken and emersed in 100 ml 0.9% saline water. The sample is left in the saline at 40 deg C, for 24 hours. An aliquot of the liquid is diluted and analysed by electrospray LC/MS/MS.

Calibration Sample 1 gram of reference monomers (eg NaAmps) are dissolved in 100 ml 0.9% saline water. An aliquot of the liquid is diluted and analysed by electrospray LC/MS/MS.

Evaluation

The concentration of the test and calibration sample are determined by linear regression analysis using a software package such as VG Mass Lynx.

EXAMPLES

All formulations detailed below were coated onto polyurethane foam (EV1700X from Caligen) at a coat weight of 0.8 to 1.6 kg per square meter and cured by exposure to ultraviolet radiation emitted from a medium pressure mercury arc lamp operating at 100 W/cm power for 10 seconds.

Example 1

Mix 6.0 g of Irgacure 184 with 20 g IRR280 (PEG400 diacrylate) from UCB (Solution A). To 0.07 g of Irgacure 184 add 23.5 g of NNDMA and stir for one hour (keep container covered from light). Add 30 g of glycerol to this and stir for 5 minutes, followed by 40 g of NaAMPS (58%). Stir for another 5 minutes. Add 0.13 g of Solution A and stir the whole formulation for 1 hour before use.

Example 2

Mix 6.0 g of Irgacure 184 with 20 g IRR280 (PEG400 diacrylate) from UCB (Solution A). To 0.07 g of Irgacure 184 add 23.5 g of NNDMA and stir for one hour (keep container covered from light). Add to this 10 g of Mowilith DM137 (50% dispersion of ethylene vinyl acetate copolymer in water from Harco) and stir for 5 minutes. Add 30 g of glycerol to this and stir for 5 minutes, followed by 40 g of NaAMPS (58%). Stir for another 5 minutes. Add 0.13 g of Solution A and stir the whole formulation for 1 hour before use.

Example 3

Mix 6.0 g of Irgacure 184 with 20 g IRR280 (PEG400 diacrylate) from UCB (Solution A). To 0.07 g of Irgacure 184 and 23.5 g of NNDMA and stir for one hour (keep container covered from light). Add to this 10 g of Mowilith DM137 (50% dispersion of ethylene vinyl acetate copolymer in water form Harco) and stir for 5 minutes. Add 30 g of glycerol to this and stir for 5 minutes, followed by 40 g of NaAMPS (58%). Stir for another 5 minutes. Add 0.5 g of Pluronic L64 (poly(ethylene glycol)—block—poly (propylene glycol)—block—poly(ethylene glycol) available from BASF). Add 0.13 g of Solution A and stir the whole formulation for 1 hour before use.

Example 4

Mix 6.0 g of Irgacure 184 with 20 g IRR280 (PEG400 diacrylate) from UCB (Solution A). To 0.07 g of Irgacure 184 add 23.4 g of NNDMA and stir for one hour (keep container covered from light). Add to this 2 g of Mowilith DM137 (50% dispersion of ethylene vinyl acetate copolymer in water from Harco) and stir for 5 minutes. Add 36 g of glycerol to this and stir for 5 minutes, followed by 40.36 g of NaAMPS (58%). Stir for another five minutes. Add 0.25 g of Pluronic L64 (poly(ethylene glycol)—block—poly (propylene glycol)—block—poly(ethylene glycol) available from BASF). To this add 0.8 g of a 30% aqueous solution of poly(styrene-alt-maleic acid) sodium salt available from Aldrich and stir for 10 minutes. Add 0.13 g of Solution A and stir the whole formulation for 1 hour before use.

Example 5

Mix 6.0 g of Irgacure 184 with 20 g IRR280 (PEG400 diacrylate) from UCB (Solution A). To 0.07 g of Irgacure 184 add 23.4 g of NNDMA and stir for one hour (keep container covered from light). Add to this 10 g of Mowilith DM137 (50% dispersion of ethylene vinyl acetate copolymer in water from Harco) and stir for 5 minutes. Add 36 g of glycerol to this and stir for 5 minutes, followed by 40.36 g of NaAMPS (58%). Stir for another 5 minutes. Add 0.25 g of Pluronic L64 (poly(ethylene glycol)—block—poly (propylene glycol)—block—poly(ethylene glycol) available from BASF). To this add 0.8 g of a 30% aqueous solution of poly(styrene-alt-maleic acid) sodium salt available form Aldrich and stir for 10 minutes. Add 0.13 g of solution A and stir the whole formulation for 1 hour before use.

Example 6

Mix 6.0 g of Irgacure 184 with 20 g IR280 (PEG400 diacrylate) from UCB (Solution A). To 0.07 g of Irgacure 184 add 23.4 g of NNDMA and stir for one hour (keep container covered from light). Add to this 10 g of Mowilith DM137 (50% dispersion of ethylene vinyl acetate copolymer in water from Harco) and stir for 5 minutes. Add 36 g of glycerol to this and stir for 5 minutes, followed by 40.36 g of NaAMPS (58%). Stir for another 5 minutes. Add 0.5 g of Pluronic L64 (poly(ethylene glycol)—block—poly (propylene glycol)—block—poly(ethylene glycol) available from ASF). To this add 0.8 g of a 30% aqueous solution of poly(styrene-alt-maleic acid) sodium salt available from Aldrich and stir for 10 minutes. Add 0.13 g of solution A and stir the whole formulation for 1 hour before use.

Example 7

Mix 6.0 g of Irgacure 184 with 20 g IRR280 (PEG400 diacrylate) from UCB (Solution A). To 0.07 g of Irgacure 184 add 23.4 g of NNDMA and stir for one hour (keep container covered from light). Add to this 20 g of Mowilith DM137 (50% dispersion of ethylene vinyl acetate copolymer in water from Harco) and stir for 5 minutes. Add 36 g of glycerol to this and stir for 5 minutes, followed by 40.36 g of NaAMPS (50%). Stir for another 5 minutes. Add 0.5 of Pluronic L64 (poly(ethylene glycol)—block—poly(propylene glycol)—block—poly(ethylene glycol) available from BASF). To this add 0.8 g of a 30% aqueous solution of poly(styrene-alt-maleic acid) sodium salt available from Aldrich and stir for 10 minutes. Add 0.13 g of solution A and stir the whole formulation for 1 our before use.

Example 8

To parts glycerol, were added 40.4 parts of a 58% solution of the sodium salt of 2-acrylamido-2-methylpropane sulphonic acid (NAAMPS) (LZ2405A) together with 0.5 parts Pluronic LF64 (BASF), and the solution stirred to ensure uniform mixing. To the solution was added 0.13 parts of solution containing 20 parts of polyethylene glycol diacrylate (PEG600) (product of UCB Chemicals marketed under the trade name designation of Ebacryl 11) in which 6 parts of 1-hydroxycyclohexyl phenyl ketone (product of Ciba and marketed under the trade name designation of Irgacure 184) had been dissolved. A promised solution of 8 parts butyl acrylate and 15.7 parts N,N-dimethylacrylamide (Kohjin) was added to that reaction mixture and this final solution cured by exposure to UV light as in example 1. Optical phase contrast microscopy showed that resultant gel to have a regularly phase-segregated surface and enhanced adhesion to skin that had previously treated with skin cream (Nivea). Results

| | Subject 1 | | | Subject 2 | | |
|---|---|---|---|---|---|---|
| Example | Dry ($P_{DI}$) | Greasy ($P_{GI}$) 1 min | 10 min | Dry ($P_{DI}$) | Greasy ($P_{GI}$) 1 min | 10 min |
| 1 | 1.75 | 0.13 | — | 1.57 | 0.19 | — |
| 2 | 2.96 | 0.16 | — | 3.18 | 0.44 | — |
| 3 | 2.81 | 0.52 | 0.33 | 2.46 | 0.67 | 0.61 |
| 4 | 0.81 | 0.15 | 0.26 | 0.96 | 0.29 | 0.47 |
| 5 | 1.2 | 0.52 | 0.69 | 2.2 | 0.83 | 0.88 |
| 6 | 1.6 | 0.45 | 0.6 | 2.2 | 0.64 | 0.56 |
| 7 | 1.2 | 0.49 | 0.62 | 1.6 | 0.74 | 0.88 |

What we claim is:

1. A disposable human waste management device comprising:
   a bag;
   said bag further comprising an aperture and a flange surrounding said aperture;
   wherein said flange further comprises a wearer facing surface and a garment facing surface opposed thereto;
   wherein an adhesive covers at least a portion of said wearer facing surface;
   wherein said adhesive has a dry peel strength ($P_{DI}$) and a greasy peel strength ($P_{GI}$); and,
   wherein the ratio of $P_{DI}$ to $P_{GI}$ ranges from 1:1 to 1:0.2.

2. The disposable human waste management device of claim 1, wherein said ratio of said dry peel strength ($P_{DI}$) to said greasy peel strength ($P_{GI}$) ranges from 1:1 to 1:0.3.

3. The disposable human waste management device of claim 1, wherein said dry peel strength, $P_{DI}$, ranges from 0.1N/cm to 5.0N/cm.

4. The disposable human waste management device of claim 3, wherein said dry peel strength, $P_{DI}$, ranges from 0.5N/cm to 3.0N/cm.

5. The disposable human waste management device of claim 1, wherein said greasy peel strength, $P_{GI}$, ranges from 0.1N/cm to 5.0N/cm.

6. The disposable human waste management device of claim 1, wherein said adhesive is provided in a layer having a thickness C;
   wherein said adhesive has a viscous modulus at a temperature of 25° C. ($G''_{25}$(100 rad/sec)); and,
   wherein said viscous modulus, $G''_{25}$ (100 rad/sec), is defined by the equation:

$$G''_{25} \leq [(7.00+C) \times 3000] Pa.$$

7. The disposable human waste management device of claim 6 wherein said viscous modulus, $G''_{25}$ (100 rad/sec), is defined by the equation:

$$G''_{25} \leq [(5.50+C) \times 1700] Pa.$$

8. The disposable human waste management device of claim 6, wherein said adhesive has an elastic modulus at a temperature of 37° C. ($G'_{37}$(1 rad/sec)), and a viscous modulus at a temperature of 37° C. ($G''_{37}$, (1 rad/sec));
   wherein $G'_{37}$(1 rad/sec) ranges from 500 Pa to 20000 Pa;
   wherein $G''_{37}$(1 rad/sec) ranges from 100 Pa to 15000 Pa; and,
   wherein the ratio $G'_{37}$(1 rad/sec)/$G''_{37}$(1 rad/sec) ranges from 1 to 30.

9. The disposable human waste management device of claim 8 wherein:
   $G'_{37}$(1 rad/sec) ranges from 700 Pa to 15000 Pa; and,
   wherein $G''_{37}$(1 rad/sec) ranges from 100 Pa to 10000 Pa.

10. The disposable human waste management device of claim 9, wherein:
    $G'_{37}$(1 rad/sec) ranges from 1000 Pa to 10000 Pa; and,
    wherein $G''_{37}$(1 rad/sec) ranges from 300 Pa to 5000 Pa.

11. The disposable human waste management device of claim 1, wherein said adhesive comprises:
    a polymer selected from the group consisting of acrylics, sulphonated polymers, vinyl alcohols, vinyl pyrrolidine, polyethylene oxide, and mixtures thereof; and,
    a plasticizer selected from the group consisting of polyhydric alcohols, polyethylene glycols, sorbitol, water, and mixtures thereof.

12. The disposable human waste management device of claim 11, wherein said adhesive further comprises at least one lipid micelling polymer.

13. The disposable human waste management device of claim 12 wherein said lipid micelling polymer is an alternating polymer of styrene and maleic anhydride.

14. The disposable human waste management device of claim 11 wherein said adhesive further comprises a surfactant.

15. The disposable human waste management device of claim 14, wherein said surfactant comprises at least one propylene oxide ethylene oxide block copolymer.

16. The disposable human waste management device of claim 11, wherein said adhesive is a hydrophilic-hydrophobic mixed phase adhesive.

17. The disposable human waste management device of claim 16, wherein the ratio of said hydrophilic components to said hydrophobic components is from 3:1 to 1:3.

18. The disposable human waste management device of claim 16, wherein said adhesive comprises a hydrophilic component selected from the group consisting of 2-acrylamide methyl-propane sulphonic acid, acrylic (3-sulphopropyl) ester acid and salts thereof, and combinations thereof; and, wherein said hydrophobic component is selected from the group consisting of acrylamide, acrylonitrite, methylacrylate, ethyl acrylate, butylacrylate, vinyl ethers, vinylpyrrolidine, gylcidyl-acrylate, methylacrylate, hydroxyethylacrylate, hyddroxypropoyl-acrylate, and combinations thereof.

19. The disposable human waste management device of claim 1, wherein said disposable human waste management device may be used in conjunction with a diaper.

* * * * *